US008017237B2

(12) United States Patent
Ludwig et al.

(10) Patent No.: US 8,017,237 B2
(45) Date of Patent: Sep. 13, 2011

(54) NANOSHELLS ON POLYMERS

(75) Inventors: Florian Niklas Ludwig, Mountain View, CA (US); Stephen D. Pacetti, San Jose, CA (US); Syed F. A. Hossainy, Fremont, CA (US); Dariush Davalian, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 901 days.

(21) Appl. No.: 11/473,822

(22) Filed: Jun. 23, 2006

(65) Prior Publication Data
US 2007/0298257 A1    Dec. 27, 2007

(51) Int. Cl.
B32B 5/16    (2006.01)
(52) U.S. Cl. ........... 428/403; 428/407; 427/212; 424/46
(58) Field of Classification Search .................. 428/403, 428/407; 427/212; 424/46
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 2,647,017 A | 7/1953 | Coulliette |
| 2,701,559 A | 2/1955 | Cooper |
| 3,288,728 A | 11/1966 | Gorham |
| 3,687,135 A | 8/1972 | Stroganov et al. |
| 3,773,737 A | 11/1973 | Goodman et al. |
| 3,839,743 A | 10/1974 | Schwarcz |
| 3,849,514 A | 11/1974 | Gray, Jr. et al. |
| 3,900,632 A | 8/1975 | Robinson |
| 4,075,045 A | 2/1978 | Rideout |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,226,243 A | 10/1980 | Shalaby et al. |
| 4,321,711 A | 3/1982 | Mano |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,902,289 A | 2/1990 | Yannas |
| 4,906,423 A | 3/1990 | Frisch |

(Continued)

FOREIGN PATENT DOCUMENTS

CA    2 008 312    7/1990
(Continued)

OTHER PUBLICATIONS

U.S. Appl. No. 10/255,913, filed Sep. 26, 2002, Tang et al. U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/409,410, filed Apr. 7, 2003, Pacetti.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905,filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003 Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Tang et al.

(Continued)

Primary Examiner — Leszek Kiliman
(74) Attorney, Agent, or Firm — Squire, Sanders & Dempsey (US) LLP

(57) ABSTRACT

Nano-constructs comprising nanoshells and methods of using the nano-constructs for treating or ameliorating a medical condition are provided.

46 Claims, No Drawings

U.S. PATENT DOCUMENTS

| | | |
|---|---|---|
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |
| 5,306,250 A | 4/1994 | March et al. |
| 5,306,286 A | 4/1994 | Stack et al. |
| 5,306,294 A | 4/1994 | Winston et al. |
| 5,306,501 A | 4/1994 | Viegas et al. |
| 5,306,786 A | 4/1994 | Moens et al. |
| 5,308,641 A | 5/1994 | Cahalan et al. |
| 5,314,472 A | 5/1994 | Fontaine |
| 5,318,531 A | 6/1994 | Leone |
| 5,328,471 A | 7/1994 | Slepian |
| 5,330,500 A | 7/1994 | Song |
| 5,330,768 A | 7/1994 | Park et al. |
| 5,336,518 A | 8/1994 | Narayanan et al. |
| 5,342,283 A | 8/1994 | Good |
| 5,342,348 A | 8/1994 | Kaplan |
| 5,342,395 A | 8/1994 | Jarrett et al. |
| 5,342,621 A | 8/1994 | Eury |
| 5,344,426 A | 9/1994 | Lau et al. |
| 5,344,455 A | 9/1994 | Keogh et al. |
| 5,350,800 A | 9/1994 | Verhoeven et al. |
| 5,356,433 A | 10/1994 | Rowland et al. |
| 5,360,401 A | 11/1994 | Turnland et al. |
| 5,360,443 A | 11/1994 | Barone et al. |
| 5,364,354 A | 11/1994 | Walker et al. |
| 5,366,504 A | 11/1994 | Andersen et al. |
| 5,368,560 A | 11/1994 | Rambo et al. |
| 5,370,684 A | 12/1994 | Vallana et al. |
| 5,380,299 A | 1/1995 | Fearnot et al. |
| 5,383,925 A | 1/1995 | Schmitt |
| 5,383,927 A | 1/1995 | DeGoicoechea et al. |
| 5,385,580 A | 1/1995 | Schmitt |
| 5,387,450 A | 2/1995 | Stewart |
| 5,389,106 A | 2/1995 | Tower |
| 5,399,666 A | 3/1995 | Ford |
| 5,405,472 A | 4/1995 | Leone |
| 5,409,495 A | 4/1995 | Osborn |
| 5,411,466 A | 5/1995 | Hess |
| 5,411,477 A | 5/1995 | Saab |
| 5,412,035 A | 5/1995 | Schmitt et al. |
| 5,415,938 A | 5/1995 | Cahalan et al. |
| 5,417,981 A | 5/1995 | Endo et al. |
| 5,423,849 A | 6/1995 | Engelson et al. |
| 5,423,885 A | 6/1995 | Williams |
| 5,429,618 A | 7/1995 | Keogh |
| 5,441,515 A | 8/1995 | Khosravi et al. |
| 5,443,458 A | 8/1995 | Eury et al. |
| 5,443,496 A | 8/1995 | Schwartz et al. |
| 5,443,500 A | 8/1995 | Sigwart |
| 5,445,646 A | 8/1995 | Euteneuer et al. |
| 5,447,724 A | 9/1995 | Helmus et al. |
| 5,451,233 A | 9/1995 | Yock |
| 5,455,040 A | 10/1995 | Marchant |
| 5,456,661 A | 10/1995 | Narciso, Jr. |
| 5,456,713 A | 10/1995 | Chuter |
| 5,458,615 A | 10/1995 | Klemm et al. |
| 5,460,610 A | 10/1995 | Don Michael |
| 5,462,990 A | 10/1995 | Hubbell et al. |
| 5,464,450 A | 11/1995 | Buscemi et al. |
| 5,464,650 A | 11/1995 | Berg et al. |
| 5,470,313 A | 11/1995 | Crocker et al. |
| 5,470,603 A | 11/1995 | Staniforth et al. |
| 5,476,476 A | 12/1995 | Hillstead |
| 5,476,509 A | 12/1995 | Keogh et al. |
| 5,485,496 A | 1/1996 | Lee et al. |
| 5,496,346 A | 3/1996 | Horzewski et al. |

| Patent Number | Date | Inventor(s) | Patent Number | Date | Inventor(s) |
|---|---|---|---|---|---|
| 5,500,013 A | 3/1996 | Buscemi et al. | 5,700,286 A | 12/1997 | Tartaglia et al. |
| 5,501,227 A | 3/1996 | Yock | 5,702,754 A | 12/1997 | Zhong |
| 5,502,158 A | 3/1996 | Sinclair et al. | 5,702,818 A | 12/1997 | Cahalan et al. |
| 5,507,768 A | 4/1996 | Lau et al. | 5,707,385 A | 1/1998 | Williams |
| 5,511,726 A | 4/1996 | Greenspan et al. | 5,711,763 A | 1/1998 | Nonami et al. |
| 5,514,154 A | 5/1996 | Lau et al. | 5,711,812 A | 1/1998 | Chapek et al. |
| 5,514,379 A | 5/1996 | Weissleder et al. | 5,711,958 A | 1/1998 | Cohn et al. |
| 5,516,560 A | 5/1996 | Harayama et al. | 5,713,949 A | 2/1998 | Jayaraman |
| 5,516,881 A | 5/1996 | Lee et al. | 5,716,981 A | 2/1998 | Hunter et al. |
| 5,527,337 A | 6/1996 | Stack et al. | 5,718,726 A | 2/1998 | Amon et al. |
| 5,537,729 A | 7/1996 | Kolobow | 5,720,726 A | 2/1998 | Marcadis et al. |
| 5,538,493 A | 7/1996 | Gerken et al. | 5,721,131 A | 2/1998 | Rudolph et al. |
| 5,545,209 A | 8/1996 | Roberts et al. | 5,722,984 A | 3/1998 | Fischell et al. |
| 5,545,408 A | 8/1996 | Trigg et al. | 5,723,219 A | 3/1998 | Kolluri et al. |
| 5,551,954 A | 9/1996 | Buscemi et al. | 5,725,549 A | 3/1998 | Lam |
| 5,554,120 A | 9/1996 | Chen et al. | 5,726,297 A | 3/1998 | Gryaznov et al. |
| 5,554,182 A | 9/1996 | Dinh et al. | 5,728,068 A | 3/1998 | Leone et al. |
| 5,556,413 A | 9/1996 | Lam | 5,728,751 A | 3/1998 | Patnaik |
| 5,558,642 A | 9/1996 | Schweich, Jr. et al. | 5,730,698 A | 3/1998 | Fischell et al. |
| 5,562,728 A | 10/1996 | Lazarus et al. | 5,733,326 A | 3/1998 | Tomonto et al. |
| 5,569,463 A | 10/1996 | Helmus et al. | 5,733,327 A | 3/1998 | Igaki et al. |
| 5,571,135 A | 11/1996 | Fraser et al. | 5,733,330 A | 3/1998 | Cox |
| 5,571,166 A | 11/1996 | Dinh et al. | 5,733,564 A | 3/1998 | Lehtinen |
| 5,571,567 A | 11/1996 | Shah | 5,733,925 A | 3/1998 | Kunz et al. |
| 5,578,046 A | 11/1996 | Liu et al. | 5,735,897 A | 4/1998 | Buirge |
| 5,578,073 A | 11/1996 | Haimovich et al. | 5,741,554 A | 4/1998 | Tisone |
| 5,584,877 A | 12/1996 | Miyake et al. | 5,741,881 A | 4/1998 | Patnaik |
| 5,588,962 A | 12/1996 | Nicholas et al. | 5,746,745 A | 5/1998 | Abele et al. |
| 5,591,199 A | 1/1997 | Porter et al. | 5,746,998 A | 5/1998 | Torchilin et al. |
| 5,591,224 A | 1/1997 | Schwartz et al. | 5,756,457 A | 5/1998 | Wang et al. |
| 5,591,227 A | 1/1997 | Dinh et al. | 5,756,476 A | 5/1998 | Epstein et al. |
| 5,591,607 A | 1/1997 | Gryaznov et al. | 5,759,205 A | 6/1998 | Valentini |
| 5,593,403 A | 1/1997 | Buscemi | 5,759,474 A | 6/1998 | Rupp et al. |
| 5,593,434 A | 1/1997 | Williams | 5,765,682 A | 6/1998 | Bley et al. |
| 5,595,722 A | 1/1997 | Grainger et al. | 5,766,204 A | 6/1998 | Porter et al. |
| 5,599,301 A | 2/1997 | Jacobs et al. | 5,766,239 A | 6/1998 | Cox |
| 5,599,307 A | 2/1997 | Bacher et al. | 5,766,710 A | 6/1998 | Turnlund et al. |
| 5,599,352 A | 2/1997 | Dinh et al. | 5,769,883 A | 6/1998 | Buscemi et al. |
| 5,599,922 A | 2/1997 | Gryaznov et al. | 5,769,884 A | 6/1998 | Solovay |
| 5,605,696 A | 2/1997 | Eury et al. | 5,770,609 A | 6/1998 | Grainger et al. |
| 5,607,442 A | 3/1997 | Fischell et al. | 5,772,864 A | 6/1998 | Møller et al. |
| 5,607,467 A | 3/1997 | Froix | 5,776,184 A | 7/1998 | Tuch |
| 5,609,629 A | 3/1997 | Fearnot et al. | 5,780,807 A | 7/1998 | Saunders |
| 5,610,241 A | 3/1997 | Lee et al. | 5,782,742 A | 7/1998 | Crocker et al. |
| 5,611,775 A | 3/1997 | Machold et al. | 5,783,657 A | 7/1998 | Pavlin et al. |
| 5,616,338 A | 4/1997 | Fox, Jr. et al. | 5,788,626 A | 8/1998 | Thompson |
| 5,618,298 A | 4/1997 | Simon | 5,788,979 A | 8/1998 | Alt et al. |
| 5,618,299 A | 4/1997 | Khosravi et al. | 5,800,392 A | 9/1998 | Racchini |
| 5,620,420 A | 4/1997 | Kriesel | 5,800,516 A | 9/1998 | Fine et al. |
| 5,624,411 A | 4/1997 | Tuch | 5,804,318 A | 9/1998 | Pinchuk et al. |
| 5,628,730 A | 5/1997 | Shapland et al. | 5,807,244 A | 9/1998 | Barot |
| 5,628,755 A | 5/1997 | Heller et al. | 5,810,871 A | 9/1998 | Tuckey et al. |
| 5,628,781 A | 5/1997 | Williams et al. | 5,810,873 A | 9/1998 | Morales |
| 5,628,785 A | 5/1997 | Schwartz et al. | 5,811,151 A | 9/1998 | Hendriks et al. |
| 5,628,786 A | 5/1997 | Banas et al. | 5,811,447 A | 9/1998 | Kunz et al. |
| 5,629,077 A | 5/1997 | Turnlund et al. | 5,820,917 A | 10/1998 | Tuch |
| 5,631,135 A | 5/1997 | Gryaznov et al. | 5,823,996 A | 10/1998 | Sparks |
| 5,632,771 A | 5/1997 | Boatman et al. | 5,824,048 A | 10/1998 | Tuch |
| 5,632,840 A | 5/1997 | Campbell | 5,824,049 A | 10/1998 | Ragheb et al. |
| 5,637,113 A | 6/1997 | Tartaglia et al. | 5,824,056 A | 10/1998 | Rosenberg |
| 5,644,020 A | 7/1997 | Timmermann et al. | 5,826,586 A | 10/1998 | Mishra et al. |
| 5,645,559 A | 7/1997 | Hachtman et al. | 5,830,178 A | 11/1998 | Jones et al. |
| 5,649,951 A | 7/1997 | Davidson | 5,830,179 A | 11/1998 | Mikus et al. |
| 5,649,977 A | 7/1997 | Campbell | 5,830,217 A | 11/1998 | Ryan |
| 5,653,691 A | 8/1997 | Rupp et al. | 5,830,461 A | 11/1998 | Billiar |
| 5,656,080 A | 8/1997 | Staniforth et al. | 5,830,879 A | 11/1998 | Isner |
| 5,656,082 A | 8/1997 | Takatsuki et al. | 5,833,644 A | 11/1998 | Zadno-Azizi et al. |
| 5,658,995 A | 8/1997 | Kohn et al. | 5,833,651 A | 11/1998 | Donovan et al. |
| 5,667,523 A | 9/1997 | Bynon et al. | 5,833,659 A | 11/1998 | Kranys |
| 5,667,767 A | 9/1997 | Greff et al. | 5,834,582 A | 11/1998 | Sinclair et al. |
| 5,667,796 A | 9/1997 | Otten | 5,836,962 A | 11/1998 | Gianotti |
| 5,670,558 A | 9/1997 | Onishi et al. | 5,836,965 A | 11/1998 | Jendersee et al. |
| 5,674,242 A | 10/1997 | Phan et al. | 5,837,008 A | 11/1998 | Berg et al. |
| 5,679,400 A | 10/1997 | Tuch | 5,837,313 A | 11/1998 | Ding et al. |
| 5,693,085 A | 12/1997 | Buirge et al. | 5,837,835 A | 11/1998 | Gryaznov et al. |
| 5,693,376 A | 12/1997 | Fetherston et al. | 5,840,009 A | 11/1998 | Fischell et al. |
| 5,695,498 A | 12/1997 | Tower | 5,840,083 A | 11/1998 | Braach-Maksvytis |
| 5,695,810 A | 12/1997 | Dubin et al. | 5,843,033 A | 12/1998 | Ropiak |
| 5,697,967 A | 12/1997 | Dinh et al. | 5,843,119 A | 12/1998 | Shmulewitz |

| Patent | Date | Inventor |
|---|---|---|
| 5,843,172 A | 12/1998 | Yan |
| 5,846,247 A | 12/1998 | Unsworth et al. |
| 5,849,859 A | 12/1998 | Acemoglu |
| 5,851,508 A | 12/1998 | Greff et al. |
| 5,853,408 A | 12/1998 | Muni |
| 5,854,207 A | 12/1998 | Lee et al. |
| 5,854,376 A | 12/1998 | Higashi |
| 5,855,598 A | 1/1999 | Pinchuk |
| 5,855,612 A | 1/1999 | Ohthuki et al. |
| 5,855,618 A | 1/1999 | Patnaik et al. |
| 5,857,998 A | 1/1999 | Barry |
| 5,858,556 A | 1/1999 | Eckert et al. |
| 5,858,746 A | 1/1999 | Hubbell et al. |
| 5,858,990 A | 1/1999 | Walsh |
| 5,860,954 A | 1/1999 | Ropiak |
| 5,865,814 A | 2/1999 | Tuch |
| 5,866,113 A | 2/1999 | Hendriks et al. |
| 5,868,781 A | 2/1999 | Killion |
| 5,869,127 A | 2/1999 | Zhong |
| 5,871,436 A | 2/1999 | Eury |
| 5,871,437 A | 2/1999 | Alt |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,874,355 A | 2/1999 | Huang et al. |
| 5,876,426 A | 3/1999 | Kume et al. |
| 5,876,433 A | 3/1999 | Lunn |
| 5,876,743 A | 3/1999 | Ibsen et al. |
| 5,877,224 A | 3/1999 | Brocchini et al. |
| 5,877,263 A | 3/1999 | Patnaik et al. |
| 5,879,713 A | 3/1999 | Roth et al. |
| 5,883,011 A | 3/1999 | Lin et al. |
| 5,888,533 A | 3/1999 | Dunn |
| 5,891,192 A | 4/1999 | Murayama et al. |
| 5,893,840 A | 4/1999 | Hull et al. |
| 5,893,852 A | 4/1999 | Morales |
| 5,895,407 A | 4/1999 | Jayaraman |
| 5,897,911 A | 4/1999 | Loeffler |
| 5,897,955 A | 4/1999 | Drumheller |
| 5,898,178 A | 4/1999 | Bunker |
| 5,902,631 A | 5/1999 | Wang et al. |
| 5,902,875 A | 5/1999 | Roby et al. |
| 5,905,168 A | 5/1999 | Dos Santos et al. |
| 5,906,759 A | 5/1999 | Richter |
| 5,910,564 A | 6/1999 | Gruning et al. |
| 5,914,182 A | 6/1999 | Drumheller |
| 5,914,387 A | 6/1999 | Roby et al. |
| 5,916,234 A | 6/1999 | Lam |
| 5,916,870 A | 6/1999 | Lee et al. |
| 5,919,893 A | 7/1999 | Roby et al. |
| 5,921,416 A | 7/1999 | Uchara |
| 5,922,005 A | 7/1999 | Richter et al. |
| 5,922,393 A | 7/1999 | Jayaraman |
| 5,925,552 A | 7/1999 | Keogh et al. |
| 5,925,720 A | 7/1999 | Kataoka et al. |
| 5,928,916 A | 7/1999 | Keogh |
| 5,932,299 A | 8/1999 | Katoot |
| 5,935,135 A | 8/1999 | Bramfitt et al. |
| 5,942,209 A | 8/1999 | Leavitt et al. |
| 5,947,993 A | 9/1999 | Morales |
| 5,948,018 A | 9/1999 | Dereume et al. |
| 5,948,428 A | 9/1999 | Lee et al. |
| 5,951,881 A | 9/1999 | Rogers et al. |
| 5,954,744 A | 9/1999 | Phan et al. |
| 5,955,509 A | 9/1999 | Webber et al. |
| 5,957,975 A | 9/1999 | Lafont et al. |
| 5,958,385 A | 9/1999 | Tondeur et al. |
| 5,962,138 A | 10/1999 | Kolluri et al. |
| 5,965,720 A | 10/1999 | Gryaznov et al. |
| 5,968,091 A | 10/1999 | Pinchuk et al. |
| 5,968,092 A | 10/1999 | Buscemi et al. |
| 5,969,422 A | 10/1999 | Ting et al. |
| 5,971,954 A | 10/1999 | Conway et al. |
| 5,972,027 A | 10/1999 | Johnson |
| 5,972,029 A | 10/1999 | Fuisz |
| 5,972,505 A | 10/1999 | Phillips et al. |
| 5,976,155 A | 11/1999 | Foreman et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,984,449 A | 11/1999 | Tajika et al. |
| 5,986,169 A | 11/1999 | Gjunter |
| 5,997,468 A | 12/1999 | Wolff et al. |
| 5,997,517 A | 12/1999 | Whitbourne |
| 6,010,445 A | 1/2000 | Armini et al. |
| 6,010,530 A | 1/2000 | Goicoechea |
| 6,010,573 A | 1/2000 | Bowlin |
| 6,011,125 A | 1/2000 | Lohmeijer et al. |
| 6,013,099 A | 1/2000 | Dinh et al. |
| 6,015,541 A | 1/2000 | Greff et al. |
| 6,019,789 A | 2/2000 | Dinh et al. |
| 6,024,918 A | 2/2000 | Hendriks et al. |
| 6,027,510 A | 2/2000 | Alt |
| 6,027,526 A | 2/2000 | Limon et al. |
| 6,030,371 A | 2/2000 | Pursley |
| 6,033,582 A | 3/2000 | Lee et al. |
| 6,033,719 A | 3/2000 | Keogh |
| 6,034,204 A | 3/2000 | Mohr et al. |
| 6,042,606 A | 3/2000 | Frantzen |
| 6,042,875 A | 3/2000 | Ding et al. |
| 6,045,899 A | 4/2000 | Wang et al. |
| 6,048,964 A | 4/2000 | Lee et al. |
| 6,051,021 A | 4/2000 | Frid |
| 6,051,576 A | 4/2000 | Ashton et al. |
| 6,051,648 A | 4/2000 | Rhee et al. |
| 6,054,553 A | 4/2000 | Groth et al. |
| 6,056,906 A | 5/2000 | Werneth et al. |
| 6,056,993 A | 5/2000 | Leidner et al. |
| 6,059,752 A | 5/2000 | Segal |
| 6,059,810 A | 5/2000 | Brown et al. |
| 6,060,451 A | 5/2000 | DiMaio et al. |
| 6,060,518 A | 5/2000 | Kabanov et al. |
| 6,063,092 A | 5/2000 | Shin |
| 6,066,156 A | 5/2000 | Yan |
| 6,071,266 A | 6/2000 | Kelley |
| 6,071,305 A | 6/2000 | Brown et al. |
| 6,074,659 A | 6/2000 | Kunz et al. |
| 6,080,099 A | 6/2000 | Slater et al. |
| 6,080,177 A | 6/2000 | Igaki et al. |
| 6,080,190 A | 6/2000 | Schwartz |
| 6,080,488 A | 6/2000 | Hostettler et al. |
| 6,083,258 A | 7/2000 | Yadav |
| 6,086,610 A | 7/2000 | Duerig et al. |
| 6,090,330 A | 7/2000 | Gawa et al. |
| 6,093,199 A | 7/2000 | Brown et al. |
| 6,093,463 A | 7/2000 | Thakrar |
| 6,096,070 A | 8/2000 | Ragheb et al. |
| 6,096,525 A | 8/2000 | Patnaik |
| 6,099,455 A | 8/2000 | Columbo et al. |
| 6,099,559 A | 8/2000 | Nolting |
| 6,099,561 A | 8/2000 | Alt |
| 6,099,562 A | 8/2000 | Ding et al. |
| 6,103,230 A | 8/2000 | Billiar et al. |
| 6,106,454 A | 8/2000 | Berg et al. |
| 6,106,530 A | 8/2000 | Harada |
| 6,106,889 A | 8/2000 | Beavers et al. |
| 6,107,416 A | 8/2000 | Patnaik et al. |
| 6,110,180 A | 8/2000 | Foreman et al. |
| 6,110,188 A | 8/2000 | Narciso, Jr. |
| 6,110,483 A | 8/2000 | Whitbourne et al. |
| 6,113,629 A | 9/2000 | Ken |
| 6,117,479 A | 9/2000 | Hogan et al. |
| 6,117,979 A | 9/2000 | Hendriks et al. |
| 6,120,477 A | 9/2000 | Campbell et al. |
| 6,120,491 A | 9/2000 | Kohn et al. |
| 6,120,535 A | 9/2000 | McDonald et al. |
| 6,120,536 A | 9/2000 | Ding et al. |
| 6,120,788 A | 9/2000 | Barrows |
| 6,120,847 A | 9/2000 | Yang et al. |
| 6,120,904 A | 9/2000 | Hostettler et al. |
| 6,121,027 A | 9/2000 | Clapper et al. |
| 6,123,712 A | 9/2000 | Di Caprio et al. |
| 6,125,523 A | 10/2000 | Brown et al. |
| 6,126,686 A | 10/2000 | Badylak et al. |
| 6,127,173 A | 10/2000 | Eckstein et al. |

| | | |
|---|---|---|
| 6,129,761 A | 10/2000 | Hubbell |
| 6,129,928 A | 10/2000 | Sarangapani et al. |
| 6,132,809 A | 10/2000 | Hynes et al. |
| 6,136,333 A | 10/2000 | Cohn et al. |
| 6,140,127 A | 10/2000 | Sprague |
| 6,140,431 A | 10/2000 | Kinker et al. |
| 6,143,354 A | 11/2000 | Koulik et al. |
| 6,143,370 A | 11/2000 | Panagiotou et al. |
| 6,149,574 A | 11/2000 | Trauthen et al. |
| 6,150,630 A | 11/2000 | Perry et al. |
| 6,153,252 A | 11/2000 | Hossainy et al. |
| 4,776,337 A | 12/2000 | Palmaz |
| 6,156,373 A | 12/2000 | Zhong et al. |
| 6,159,227 A | 12/2000 | Di Caprio et al. |
| 6,159,229 A | 12/2000 | Jendersee et al. |
| 6,159,951 A | 12/2000 | Karpeisky et al. |
| 6,159,978 A | 12/2000 | Myers et al. |
| 6,160,084 A | 12/2000 | Langer et al. |
| 6,165,212 A | 12/2000 | Dereume et al. |
| 6,166,130 A | 12/2000 | Rhee et al. |
| 6,168,617 B1 | 1/2001 | Blaeser et al. |
| 6,168,619 B1 | 1/2001 | Dinh et al. |
| 6,169,170 B1 | 1/2001 | Gryaznov et al. |
| 6,171,609 B1 | 1/2001 | Kunz |
| 6,172,167 B1 | 1/2001 | Stapert et al. |
| 6,174,316 B1 | 1/2001 | Tuckey et al. |
| 6,174,330 B1 | 1/2001 | Stinson |
| 6,177,523 B1 | 1/2001 | Reich et al. |
| 6,180,632 B1 | 1/2001 | Myers et al. |
| 6,183,505 B1 | 2/2001 | Mohn, Jr. et al. |
| 6,187,045 B1 | 2/2001 | Fehring et al. |
| 6,193,727 B1 | 2/2001 | Foreman et al. |
| 6,203,551 B1 | 3/2001 | Wu |
| 6,209,621 B1 | 4/2001 | Treacy |
| 6,210,715 B1 | 4/2001 | Starling et al. |
| 6,211,249 B1 | 4/2001 | Cohn et al. |
| 6,214,115 B1 | 4/2001 | Taylor et al. |
| 6,214,407 B1 | 4/2001 | Laube et al. |
| 6,214,901 B1 | 4/2001 | Chudzik et al. |
| 6,217,586 B1 | 4/2001 | Mackenzie |
| 6,217,721 B1 | 4/2001 | Xu et al. |
| 6,224,626 B1 | 5/2001 | Steinke |
| 6,224,675 B1 | 5/2001 | Prentice et al. |
| 6,224,894 B1 | 5/2001 | Jamiolkowski et al. |
| 6,228,845 B1 | 5/2001 | Donovan et al. |
| 6,231,590 B1 | 5/2001 | Slaikeu et al. |
| 6,231,600 B1 | 5/2001 | Zhong |
| 6,240,616 B1 | 6/2001 | Yan |
| 6,242,041 B1 | 6/2001 | Katoot et al. |
| 6,245,076 B1 | 6/2001 | Yan |
| 6,245,099 B1 | 6/2001 | Edwin et al. |
| 6,245,103 B1 | 6/2001 | Stinson |
| 6,245,753 B1 | 6/2001 | Byun et al. |
| 6,245,760 B1 | 6/2001 | He et al. |
| 6,248,129 B1 | 6/2001 | Froix |
| 6,248,344 B1 | 6/2001 | Ylanen et al. |
| 6,251,135 B1 | 6/2001 | Stinson et al. |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,850 B1 | 8/2001 | Gambale |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. |
| 6,327,772 B1 | 12/2001 | Zadno-Azizi et al. |
| 6,331,313 B1 | 12/2001 | Wong et al. |
| 4,733,665 C2 | 1/2002 | Palmaz |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. |
| 6,375,458 B1 | 4/2002 | Moorleghem et al. |
| 6,375,826 B1 | 4/2002 | Wang et al. |
| 6,379,379 B1 | 4/2002 | Wang |
| 6,379,381 B1 | 4/2002 | Hossainy et al. |
| 6,387,118 B1 | 5/2002 | Hanson |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 | 7/2002 | Yang et al. |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,475,779 B2 | 11/2002 | Mathiowitz et al. |
| 6,479,565 B1 | 11/2002 | Stanley |
| 6,481,262 B1 | 11/2002 | Ching et al. |
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |

| Patent No. | Date | Inventor |
|---|---|---|
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. |
| 6,569,191 B1 | 5/2003 | Hogan |
| 6,569,193 B1 | 5/2003 | Cox et al. |
| 6,572,644 B1 | 6/2003 | Moein |
| 6,572,672 B2 | 6/2003 | Yadav et al. |
| 6,574,851 B1 | 6/2003 | Mirizzi |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal |
| 6,605,874 B2 | 8/2003 | Leu et al. |
| 6,610,087 B1 | 8/2003 | Zarbatany et al. |
| 6,613,072 B2 | 9/2003 | Lau et al. |
| 6,613,432 B2 | 9/2003 | Zamora et al. |
| 6,616,765 B1 | 9/2003 | Castro et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,641,611 B2 | 11/2003 | Jayaraman |
| 6,645,135 B1 | 11/2003 | Bhat |
| 6,645,195 B1 | 11/2003 | Bhat et al. |
| 6,645,243 B2 | 11/2003 | Vallana et al. |
| 6,645,547 B1 | 11/2003 | Shekalim et al. |
| 6,656,162 B2 | 12/2003 | Santini, Jr. et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,660,381 B2 | 12/2003 | Halas et al. |
| 6,663,662 B2 | 12/2003 | Pacetti et al. |
| 6,663,880 B1 | 12/2003 | Roorda et al. |
| 6,664,187 B1 | 12/2003 | Ngo et al. |
| 6,664,335 B2 | 12/2003 | Krishnan |
| 6,666,214 B2 | 12/2003 | Canham |
| 6,666,880 B1 | 12/2003 | Chiu et al. |
| 6,667,049 B2 | 12/2003 | Janas et al. |
| 6,669,723 B2 | 12/2003 | Killion et al. |
| 6,669,980 B2 | 12/2003 | Hansen |
| 6,673,154 B1 | 1/2004 | Pacetti et al. |
| 6,673,385 B1 | 1/2004 | Ding et al. |
| 6,676,697 B1 | 1/2004 | Richter |
| 6,676,700 B1 | 1/2004 | Jacobs et al. |
| 6,679,980 B1 | 1/2004 | Andreacchi |
| 6,685,986 B2 * | 2/2004 | Oldenburg et al. ........... 427/214 |
| 6,689,099 B2 | 2/2004 | Mirzaee |
| 6,689,350 B2 | 2/2004 | Uhrich |
| 6,689,375 B1 | 2/2004 | Wahlig et al. |
| 6,695,920 B1 | 2/2004 | Pacetti et al. |
| 6,699,281 B2 | 3/2004 | Vallana et al. |
| 6,699,724 B1 * | 3/2004 | West et al. .................... 436/525 |
| 6,703,307 B2 | 3/2004 | Lopatin et al. |
| 6,706,013 B1 | 3/2004 | Bhat et al. |
| 6,706,273 B1 | 3/2004 | Roessler |
| 6,709,379 B1 | 3/2004 | Brandau et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,723,120 B2 | 4/2004 | Yan |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,752,826 B2 | 6/2004 | Holloway et al. |
| 6,753,007 B2 | 6/2004 | Haggard et al. |
| 6,753,071 B1 | 6/2004 | Pacetti |
| 6,758,859 B1 | 7/2004 | Dang et al. |
| 6,759,054 B2 | 7/2004 | Chen et al. |
| 6,764,505 B1 | 7/2004 | Hossainy et al. |
| 6,774,278 B1 | 8/2004 | Ragheb et al. |
| 6,776,792 B1 | 8/2004 | Yan et al. |
| 6,776,796 B2 | 8/2004 | Falotico et al. |
| 6,780,424 B2 | 8/2004 | Claude |
| 6,783,793 B1 | 8/2004 | Hossainy et al. |
| 6,790,228 B2 | 9/2004 | Hossainy et al. |
| 6,818,063 B1 | 11/2004 | Kerrigan |
| 6,824,559 B2 | 11/2004 | Michal |
| 6,846,323 B2 | 1/2005 | Yip et al. |
| 6,860,946 B2 | 3/2005 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 7,008,667 B2 | 3/2006 | Chudzik et al. |
| 2001/0007083 A1 | 7/2001 | Roorda |
| 2001/0014717 A1 | 8/2001 | Hossainy et al. |
| 2001/0016753 A1 | 8/2001 | Caprio et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0044652 A1 | 11/2001 | Moore |
| 2001/0051608 A1 | 12/2001 | Mathiowitz et al. |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0061363 A1 | 5/2002 | Halas et al. |
| 2002/0062148 A1 | 5/2002 | Hart |
| 2002/0065553 A1 | 5/2002 | Weber |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0116050 A1 | 8/2002 | Kocur |
| 2002/0120326 A1 | 8/2002 | Michal |
| 2002/0132045 A1 | 9/2002 | Halas et al. |
| 2002/0138133 A1 | 9/2002 | Lenz et al. |
| 2002/0142039 A1 | 10/2002 | Claude |
| 2002/0155212 A1 | 10/2002 | Hossainy |
| 2002/0161114 A1 | 10/2002 | Gunatillake et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0187347 A1 | 12/2002 | Halas |
| 2002/0187632 A1 | 12/2002 | Marsh |
| 2002/0188037 A1 | 12/2002 | Chudzik et al. |
| 2002/0188277 A1 | 12/2002 | Roorda et al. |
| 2003/0003221 A1 | 1/2003 | Zhong et al. |
| 2003/0004141 A1 | 1/2003 | Brown |
| 2003/0028243 A1 | 2/2003 | Bates et al. |

| | | | | | | |
|---|---|---|---|---|---|---|
| 2003/0028244 A1 | 2/2003 | Bates et al. | | 2005/0055078 A1 | 3/2005 | Campbell |
| 2003/0031780 A1 | 2/2003 | Chudzik et al. | | 2005/0056118 A1 | 3/2005 | Xia et al. |
| 2003/0032767 A1 | 2/2003 | Tada et al. | | 2005/0060020 A1 | 3/2005 | Jenson |
| 2003/0033001 A1 | 2/2003 | Igaki | | 2005/0064088 A1 | 3/2005 | Fredrickson |
| 2003/0036794 A1 | 2/2003 | Ragheb et al. | | 2005/0065501 A1 | 3/2005 | Wallace |
| 2003/0039689 A1 | 2/2003 | Chen et al. | | 2005/0065545 A1 | 3/2005 | Wallace |
| 2003/0040712 A1 | 2/2003 | Ray et al. | | 2005/0065593 A1 | 3/2005 | Chu et al. |
| 2003/0040790 A1 | 2/2003 | Furst | | 2005/0074406 A1 | 4/2005 | Couvillon, Jr. et al. |
| 2003/0054090 A1 | 3/2003 | Hansen | | 2005/0074545 A1 | 4/2005 | Thomas |
| 2003/0055482 A1 | 3/2003 | Schwager et al. | | 2005/0075714 A1 | 4/2005 | Cheng et al. |
| 2003/0059520 A1 | 3/2003 | Chen et al. | | 2005/0079274 A1 | 4/2005 | Palasis et al. |
| 2003/0060877 A1 | 3/2003 | Falotico et al. | | 2005/0084515 A1 | 4/2005 | Udipi et al. |
| 2003/0065377 A1 | 4/2003 | Davila et al. | | 2005/0106210 A1 | 5/2005 | Ding et al. |
| 2003/0072868 A1 | 4/2003 | Harish et al. | | 2005/0113903 A1 | 5/2005 | Rosenthal et al. |
| 2003/0073961 A1 | 4/2003 | Happ | | 2006/0079454 A1 | 4/2006 | Reches et al. |
| 2003/0083646 A1 | 5/2003 | Sirhan et al. | | 2007/0014752 A1* | 1/2007 | Roy et al. .................. 424/78.08 |
| 2003/0083739 A1 | 5/2003 | Cafferata | | 2007/0053845 A1* | 3/2007 | Sengupta et al. ............... 424/46 |
| 2003/0088307 A1 | 5/2003 | Shulze et al. | | 2007/0292518 A1* | 12/2007 | Ludwig ........................ 424/489 |
| 2003/0093107 A1 | 5/2003 | Parsonage et al. | | | | |
| 2003/0097088 A1 | 5/2003 | Pacetti | | FOREIGN PATENT DOCUMENTS | | |
| 2003/0097173 A1 | 5/2003 | Dutta | | | | |
| 2003/0099630 A1* | 5/2003 | DiBenedetto et al. ..... 424/94.64 | | CA | 2 007 648 | 4/1991 |
| 2003/0099712 A1 | 5/2003 | Jayaraman | | CA | 1 322 628 | 10/1993 |
| 2003/0100865 A1 | 5/2003 | Santini, Jr. et al. | | CA | 1 336 319 | 7/1995 |
| 2003/0105518 A1 | 6/2003 | Dutta | | CA | 1 338 303 | 5/1996 |
| 2003/0105530 A1 | 6/2003 | Pirhonen | | DE | 042 24 401 | 1/1994 |
| 2003/0113439 A1 | 6/2003 | Pacetti et al. | | DE | 044 07 079 | 9/1994 |
| 2003/0113445 A1 | 6/2003 | Martin | | DE | 197 31 021 | 1/1999 |
| 2003/0138487 A1 | 7/2003 | Hogan et al. | | DE | 199 16 086 | 10/1999 |
| 2003/0150380 A1 | 8/2003 | Yoe | | DE | 198 56 983 | 12/1999 |
| 2003/0157241 A1 | 8/2003 | Hossainy et al. | | EP | 0 108 171 | 5/1984 |
| 2003/0158517 A1 | 8/2003 | Kokish | | EP | 0 144 534 | 6/1985 |
| 2003/0164064 A1 | 9/2003 | Halas et al. | | EP | 0 301 856 | 2/1989 |
| 2003/0171053 A1 | 9/2003 | Sanders | | EP | 0 380 668 | 4/1989 |
| 2003/0185964 A1 | 10/2003 | Weber et al. | | EP | 0 351 314 | 1/1990 |
| 2003/0187495 A1 | 10/2003 | Cully et al. | | EP | 0 364 787 | 4/1990 |
| 2003/0190406 A1 | 10/2003 | Hossainy et al. | | EP | 0 396 429 | 11/1990 |
| 2003/0203617 A1 | 10/2003 | Lane et al. | | EP | 0 397 500 | 11/1990 |
| 2003/0207020 A1 | 11/2003 | Villareal | | EP | 0 464 755 | 1/1992 |
| 2003/0208259 A1 | 11/2003 | Penhasi | | EP | 0 493 788 | 7/1992 |
| 2003/0209835 A1 | 11/2003 | Chun et al. | | EP | 0 526 606 | 9/1992 |
| 2003/0211230 A1 | 11/2003 | Pacetti et al. | | EP | 0 514 406 | 11/1992 |
| 2003/0226833 A1 | 12/2003 | Shapovalov et al. | | EP | 0 517 075 | 12/1992 |
| 2003/0236565 A1 | 12/2003 | DiMatteo et al. | | EP | 0 540 290 | 5/1993 |
| 2004/0018296 A1 | 1/2004 | Castro et al. | | EP | 0 553 960 | 8/1993 |
| 2004/0029952 A1 | 2/2004 | Chen et al. | | EP | 0 554 082 | 8/1993 |
| 2004/0047978 A1 | 3/2004 | Hossainy et al. | | EP | 0 565 251 | 10/1993 |
| 2004/0047980 A1 | 3/2004 | Pacetti et al. | | EP | 0 578 998 | 1/1994 |
| 2004/0052858 A1 | 3/2004 | Wu et al. | | EP | 0 604 022 | 6/1994 |
| 2004/0052859 A1 | 3/2004 | Wu et al. | | EP | 0 621 017 | 10/1994 |
| 2004/0054104 A1 | 3/2004 | Pacetti | | EP | 0 623 354 | 11/1994 |
| 2004/0060508 A1 | 4/2004 | Pacetti et al. | | EP | 0 627 226 | 12/1994 |
| 2004/0062853 A1 | 4/2004 | Pacetti et al. | | EP | 0 649 637 | 4/1995 |
| 2004/0063805 A1 | 4/2004 | Pacetti et al. | | EP | 0 665 023 | 8/1995 |
| 2004/0071861 A1 | 4/2004 | Mandrusov et al. | | EP | 0 701 802 | 3/1996 |
| 2004/0072922 A1 | 4/2004 | Hossainy et al. | | EP | 0 701 803 | 3/1996 |
| 2004/0073298 A1 | 4/2004 | Hossainy | | EP | 0 709 068 | 5/1996 |
| 2004/0086542 A1 | 5/2004 | Hossainy et al. | | EP | 0 716 836 | 6/1996 |
| 2004/0086550 A1 | 5/2004 | Roorda et al. | | EP | 0 732 087 | 9/1996 |
| 2004/0093077 A1 | 5/2004 | White et al. | | EP | 0 832 618 | 9/1996 |
| 2004/0096504 A1 | 5/2004 | Michal | | EP | 0 756 853 | 2/1997 |
| 2004/0098095 A1 | 5/2004 | Burnside et al. | | EP | 0 809 999 | 12/1997 |
| 2004/0098117 A1 | 5/2004 | Hossainy et al. | | EP | 0 832 655 | 4/1998 |
| 2004/0111149 A1 | 6/2004 | Stinson | | EP | 0 834 293 | 4/1998 |
| 2004/0127970 A1 | 7/2004 | Saunders | | EP | 0 850 604 | 7/1998 |
| 2004/0142015 A1 | 7/2004 | Hossainy et al. | | EP | 0 850 651 | 7/1998 |
| 2004/0143317 A1 | 7/2004 | Stinson et al. | | EP | 0 879 595 | 11/1998 |
| 2004/0167610 A1 | 8/2004 | Fleming, III | | EP | 0 910 584 | 4/1999 |
| 2004/0213893 A1 | 10/2004 | Boulais | | EP | 0 923 953 | 6/1999 |
| 2004/0236417 A1 | 11/2004 | Yan et al. | | EP | 0 953 320 | 11/1999 |
| 2004/0265475 A1 | 12/2004 | Hossainy | | EP | 0 970 711 | 1/2000 |
| 2005/0037052 A1 | 2/2005 | Udipi et al. | | EP | 0 972 498 | 1/2000 |
| 2005/0038134 A1 | 2/2005 | Loomis et al. | | EP | 0 974 315 | 1/2000 |
| 2005/0038497 A1 | 2/2005 | Neuendorf et al. | | EP | 0 982 041 | 3/2000 |
| 2005/0043786 A1 | 2/2005 | Chu et al. | | EP | 1 023 879 | 8/2000 |
| 2005/0049693 A1 | 3/2005 | Walker | | EP | 1 034 752 | 9/2000 |
| 2005/0049694 A1 | 3/2005 | Neary | | EP | 1 075 838 | 2/2001 |
| 2005/0054774 A1 | 3/2005 | Kangas | | EP | 1 103 234 | 5/2001 |
| 2005/0055044 A1 | 3/2005 | Kangas | | EP | 1 192 957 | 4/2002 |
| | | | | EP | 1 273 314 | 1/2003 |

| | | |
|---|---|---|
| EP | 0 869 847 | 3/2003 |
| EP | 0 941 072 | 1/2004 |
| FR | 2 753 907 | 4/1998 |
| GB | 2 247 696 | 3/1992 |
| GB | 2 316 086 | 1/2000 |
| GB | 2 316 342 | 1/2000 |
| GB | 2 333 975 | 1/2000 |
| GB | 2 336 551 | 1/2000 |
| GB | 2 356 586 | 5/2001 |
| GB | 2 356 587 | 5/2001 |
| GB | 2 333 474 | 6/2001 |
| GB | 2 334 685 | 6/2001 |
| GB | 2 356 585 | 7/2001 |
| GB | 2 374 302 | 8/2001 |
| GB | 2 370 243 | 6/2002 |
| GB | 2 384 199 | 7/2003 |
| JP | SHO49-48336 | 12/1974 |
| JP | SHO54-1831O | 7/1979 |
| JP | SHO60-28504 | 7/1985 |
| JP | 21199867 | 5/1994 |
| JP | HEI8-33718 | 2/1996 |
| JP | HEI10-151190 | 6/1998 |
| JP | 2919971 B2 | 7/1999 |
| JP | 2001-190687 | 7/2001 |
| SU | 0872531 | 10/1981 |
| SU | 0876663 | 10/1981 |
| SU | 0905228 | 2/1982 |
| SU | 0790725 | 2/1983 |
| SU | 1016314 | 5/1983 |
| SU | 0811750 | 9/1983 |
| SU | 1293518 | 2/1987 |
| SU | 1477423 | 5/1989 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/11176 | 8/1991 |
| WO | WO 91/12846 | 9/1991 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/09760 | 5/1994 |
| WO | WO 94/21196 | 9/1994 |
| WO | WO 95/10989 | 4/1995 |
| WO | WO 95/11817 | 5/1995 |
| WO | WO 95/24929 | 9/1995 |
| WO | WO 95/29647 | 11/1995 |
| WO | WO 95/33422 | 12/1995 |
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/46351 | 9/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/05586 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

U.S. Appl. No. 10/851,411, filed May 20, 2004, Chen.
U.S. Appl. No. 10/855,294, filed May 26, 2004, Pacetti et al.
U.S. Appl. No. 10/877,527, filed Jun. 24, 2004, Yan et al.
U.S. Appl. No. 10/897,244, filed Jul. 21, 2004, Hossainy et al.
U.S. Appl. No. 10/928,587, filed Aug. 26, 2004, Hossainy et al.
U.S. Appl. No. 10/931,853, filed Aug. 31, 2004, Hossainy et al.
U.S. Appl. No. 10/932,364, filed Aug. 31, 2004, Foreman et al.
U.S. Appl. No. 11/015,313, filed Dec. 16, 2004, Pacetti et al.
U.S. Appl. No. 11/093,166, filed Mar. 28, 2005, Kerrigan.
U.S. Appl. No. 11/115,631, filed Apr. 26, 2005, Chen.
U.S. Appl. No. 11/119,020, filed Apr. 29, 2005, Hossainy et al.
U.S. Appl. No. 11/187,467, filed Jul. 22, 2005, Desnoyer et al.
U.S. Appl. No. 11/453,704, filed Jun. 14, 2006, Ludwig.
U.S. Appl. No. 11/454,813, filed Jun. 15, 2006, Ludwig et al.
Angioplasty.org., *Balloons and Stents*, http://www.ptca.orq/devices04.html, printed Oct. 15, 2004, 2 pages.
Anonymous, *Bioabsorbable stent mounted on a catheter having optical coherence tomography capabilities*, Research Disclosure, pp. 1159-1162 (Sep. 2004).
Anonymous, *Capillary Action*, http://www.ndt-ed.org/EducationResources/CommunityCollege/PenetrantTest/Introduction/Keywords/pt1.htm, printed Aug. 12, 2005, 1 page.
Anonymous, *Capillary Force Lithography (CFL)*, Nano Processing and Organic Devices Lab, 2 pages (no date).
Anonymous, *Capillary Rise of Liquid in Different Vanes Under Variable Residual Acceleration*, http://www.zarm.uni-bremen.de/2forschung/grenzph/isoterm/cap_rise/kapst_en.htm, ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?req=1061848202959, printed Aug. 25, 2003, 2 pages.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gap Coating (Knife Over Roll, etc.)*, http://www.ferron-magnetic.co.uk/coatings/knife.htm, printed Jul. 1, 2003, 1 page.

Anonymous, *Coating Techniques, Gravure Coating*, http://www.ferron-magnetic.co.uk/coatings/gravure.htm, printed Jul. 1, 2003, 2 pages.

Anonymous, *Coating Techniques, Reverse Roll Coating*, http://www.ferron-magnetic.co.uk/coatings/revroll.htm, printed Jul. 1, 2003, 22 pages.

Anonymous, *Heparin-coated stents cut complications By 30%*, Clinica 732, pp. 17 (Nov. 18, 1996), http://www.dialogweb.com/cgi/document?req=1061847871753 printed Aug. 25, 2003, 2 pages.

Anonymous, *Liquid Gravity Motor*, http://w__ww.drspark86.com/idea001.html, printed Jun. 24, 2003, 2 pages (no date).

Anonymous, *Porosimetry—Why characterize the porosity?* 42 pages (no date.).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting Continues to Dominate Cardiology*, http://www.dialogweb.com/cgi/document?req=1061848017752, Clinica vol. 720, pp. 22 (Sep. 2, 1996), printed Aug. 25, 2003, 2 pages.

Anonymous, *Surface Energy (Surface Wetting Capability)*, http://www.ndt-ed.org/EducationResources/CommunityCollege/PenetrantTest/PTMaterials/surfaceenergy.htm, printed Apr. 6, 2004, 3 pages (no date).

Anonymous, *The 14th International Young Physicists Tournament, The winning report*, Research Center for Quantum Information, Slovak Academy of Sciences, 5 pages (no date).

Anonymous, *The Wicking Well System*, http://www.decorative.com/wicking.html, printed Jun. 24, 2003, 1 page.

Anonymous, *Typical Parylene Properties*, 3 pages (no date).

Anonymous, *Viscosity*, Commonwealth of Australia, 7 pages (no date).

Ansari, *End-to-End Tubal Anastomosis Using an Absorbable Stent*, Fertility and Sterility, vol. 32, No. 2, pp. 197-201 (Aug. 1979).

Ansari, *Tubal Reanastomosis Using Absorbable Stent*, International Journal of Fertility, vol. 23, No. 4, pp. 242-243 (1978).

Aoyagi et al., *Preparation of cross-linked aliphatic polyester and application to thermo-responsive material*, Journal of Controlled Release 32, pp. 87-96 (1994).

Barath et al., *Low Dose of Antitumor Agents Prevents Smooth Muscle Cell Proliferation After Endothelial Injury*, JACC vol. 3, No. 2, pp. 252A (Feb. 1989).

Barbucci et al., *Coating of commercially available materials with a new heparinizable Material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).

Boston Scientific, Express 2™ *Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Colombo et al., *Intracoronary Stenting Without Anticoagulation Accomplished with Intravascular Ultrasound Guidance*, Circulation vol. 91, No. 6, 1676-1688 (1995).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar. /Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischel et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx VELOCITY™ Stent*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, *ACS RX MULTI-LINK™ Coronary Stent System*, 6 pages (no date).

Guidant, *GUIDANT MULTI-LINK VISION OTW Coronary Stent System*, 2 pages (no date).

Hahn et al., *Biocompatibility of Glow-Discharge-Polmerized Films and Vacuum-Deposited Parylene*, Journal of Applied Polymer Science: Applied Polymer Symposium 38, 55-64 (1984).
Hahn et al., *Glow Discharge Polymers as Coatings for Implanted Devices*, John M. Dalton Research Center, University of Missouri-Columbia and the Graduate Center for Materials Research, pp. 109-113 (1981).
He et al., *Assessment of Tissue Blood Flow Following Small Artery Welding with an Intraluminal Dissolvable Stent*, Microsurgery, vol. 19, No. 3, pp. 148-152 (1999).
Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol., vol. 3, pp. 197-199 (1998).
Hollahan et al., *Attachment of Amino Groups to Polymer Surfaces by Radiofrequency Plasmas*, Journal of Applied Polymer Science, vol. 13, pp. 807-816 (1969).
Huang et al., *Biodegradable Polymers Derived from Aminoacids*, Macromol. Symp. 144, 7-32 (1999).
Impulse Jetting, *About Us*, http://www.impulseiettinq.com/about.html, printed Dec. 18, 2000, 1 page.
Impulse Jetting, *Our Technology*, http://www.imoulsejetting.com/tech1.html, printed Dec. 18, 2000, 1 page.
Inagaki et al., *Hydrophilic Surface Modification of Polyethylene by No-Plasma Treatment*, Adhesion Sci. Technol., vol. 4, No. 2, pp. 99-107 (1990).
Inoue et al., *An AB block copolymer of oligo(methyl methacrylate) and poly(acrylic acid) for micellar delivery of hydrophobic drugs*, Journal of Controlled Release, vol. 51, pp. 221-229 (1998).
International Search Report and Written Opinion of WIPO Application No. WIPO/US2004/026137 filed Aug. 11, 2004 (Jan. 31, 2005).
Itabashi et al., *Electroless Deposited CoWB for Copper Diffusion Barrier Metal*, International Interconnect Technology Conference, pp. 285-287 (2002).
John Ritchie Production Group, *Production of Stents* (presentation), 15 pages (Apr. 24, 2003).
Kataoka et al., *Block Copolymer Micelles as Vehicles for Drug Delivery*, Journal of Controlled Release vol. 24, pp. 119-132 (1993).
Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarbolic Acids*, Journal of Polymer Science, Part A: Polymer Chemistry, vol. 37, 391-407 (1999).
Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).
Kelley et al., *Totally Resorbable High-Strength Composite Material*, Advances in Biomedical Polymers, vol. 35, pp. 75-85 (1987).
Klocke et al, *How Soil Holds Water* (G90-964), http://ianrpubs.unl.edu/fieldcrops/g964.htm, printed Apr. 6, 2004, 9 pages.
Konopka, *In-Plane Moisture Transport in Nonwovens*, Nonwovens Cooperative Research Center, NC State University, 56 pages (no date).
Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).
Kubies et al., *Microdomain Structure In polylactide-block-poly(ethylene oxide) copolymer films*, Biomaterials, vol. 21, pp. 529-536 (2000).
Kutryk et al., *Coronary Stenting: Current Perspectives, a companion to the Handbook of Coronary Stents*, 16 pages (1999).
Lambert et al., *Localized Arterial Wall Drug Delivery From a Polymer-Coated Removable Metallic Stent*, Circulation, vol. 90, No. 2, pp. 1003-1011 (Aug. 1994).
Lemos et al., *Coronary Restenosis After Sirolimus-Eluting Stent Implantation*, Circulation, vol. 108, No. 3, pp. 257-260 (Jul. 22, 2003).

Levy et al., *Strategies For Treating Arterial Restenosis Using Polymeric Controlled Release Implants*, Biotechnology and Bioactive Polymers, pp. 259-268 (1994).
Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).
Liu et al., *Drug Release Characteristics of Unimolecular Polymeric Micelles*, Journal of Controlled Release, vol. 68, pp. 167-174 (2000).
Loeb et al., *Parylene as a Chronically Stable, Reproducible Microelectrode Insulator*, IEEE Transactions on Biomedical Engineering, pp. 121-128 (Mar. 1977).
Loh et al., *Plasma Enhanced Parylene Deposition*, Antec, pp. 1099-1103 (1991).
Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, • printed Nov. 21, 2003 (2 pgs.).
Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.
Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).
Malik et al., *Overview of plasma source ion implantation research at University of Wisconsin-Madison*, J. Vac. Sci. Technol. B, No. 12, vol. 2, pp. 843-849 (Mar./Apr. 1994).
Malik et al., *Sheath dynamics and dose analysis for planar targets in plasma source ion implantation*, Plasma Sources Sci. Technol. vol. 2, pp. 81-85 (1993).
Marconi et al., *Covalent bonding of heparin to a vinyl copolymer for biomedical applications*, Biomaterials, vol. 18, No. 12, pp. 885-890 (1997).
Martin et al., *Enhancing the biological activity of immobilized osteopontin using a type-1 collagen affinity coating*, J. Biomed. Mater. Res., vol. 70A, pp. 10-19 (May 14, 2004).
Matsumaru et al., *Embolic Materials For Endovascular Treatment of Cerebral Lesions*, J. Biomater. Sci. Polymer Edn., vol. 8, No. 7, pp. 555-569 (1997).
Mauduit et al., *Hydrolytic degradation of films prepared from blends of high and low molecular weight poly(DL-lactic acid)s*, J. Biomed. Mater. Res., vol. 30, pp. 201-207 (1996).
Meissner et al., *Intravascular Optical Coherence Tomography: Comparison with Histopathology in Atherosclerotic Peripheral Artery Specimens*, Opt. Coherence Tomography vs Histopthology in Atherosclerosis vol. 17, No. 2 pp. 343-349 (2006).
Middleton et al., *Synthetic biodegradable polymers as orthopedic devices*, Biomaterials, vol. 21, pp. 2335-2346 (2000).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).
Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).
Moody, *Vacuum Coating Ultrasonic Transducers*, 1 page, Sensors (Dec. 1993).
Muller et al., *Advances in Coronary Angioplasty: Endovascular Stents*, Coronary Artery Disease, vol. 1, No. 4., pp. 438-448 (Jul./Aug. 1990).
Musyanovych et al., *Grafting of Amino functional Monomer onto Initiator-Modified Polystyrene Particles*, Longmuir 2005, 21, pp. 2209-2217 (2004).
Neimark et al., *Hierarchical Pore Structure and Wetting Properties of Single-Wall Carbon Nanotube Fibers*, Nano Letters, vol. 3, No. 3, pp. 419-423 (2003).
Nichols et al., *Electrical Insulation of Implantable Devices by Composite Polymer Coatings*, ISA Transactions, vol. 26, No. 4, pp. 15-18 (1987).
Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).
Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).
Oldenburg et al., *Nanoengineering of optical resonances*, Chem. Physics Letters 288, pp. 243-247 (1998).
Oldenburg et al., *Infrared extinction properties of gold nanoshells*, Applied Physics Letters, vol. 75, No. 19, pp. 2897-2899 (1999).
Olson, *Parylene, a Biostabel Coating for Medical Applications*, Specialty Coating Systems, Inc. Nova Tran™ Parylene Coating Services (no date).
Ozaki et al., *New Stent Technologies*, Progress in Cardiovascular Diseases, vol. XXXIX, No. 2, pp. 129-140 (Sep./Oct. 1996).
Para Tech Coating Company, *Galxyl, Parylene Coatings by Para Tech*, 1 page (no date).
Para Tech Coating Company, *Lab Top® Parylene Deposition System*, 2 pages (no date).
Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).
Peng et al., *Role of polymers in improving the results of stenting in coronary arteries*, Biomaterial, vol. 17, pp. 685-694 (1996).
Peuster et al., *A novel approach to temporary stenting: degradable cardiovascular stents produced from corrodible metal-results 6-18 months after implantation into New Zealand white rabbits*, Heart vol. 86, pp. 563-569 (2001).
Pietrzak et al., *Bioabsorbable Fixation Devices: Status for the Craniomaxillofacial Surgeon*, Journal of Craniofacial Surgery, vol. 8, No. 2, pp. 92-96 (1997).
Pietrzak et al., *Bioresorbable Implants—Practical Considerations*, Bone, vol. 19, No. 1, Supplement, pp. 109S-119S (Jul. 1996).
Poncin-Epaillard et al., *Reactivity of a Polypropylene Surface Modified in a Nitrogen Plasma*, Plasma Surface Modification of Polymers pp. 167-180 (1994).
Prabhu, *Computational Modeling in Stent-based Drug Delivery*, Business Briefing: Medical Device Manufacturing & Technology, 4 pages (2004).
Prakash et al., *Electrophilic Modification of Polystyrene Nanospheres*, J. of Nanoscience and Nanotechnology, vol. 5, pp. 397-403 (2005).
Ramos et al., *Modeling the emulsion polymerization of amino-functionalized latex particles*, Polymer 47 pp. 1405-1413 (2006).
Ramos et al., *Polymeric and Colloidal Features of Latex Particles with surface Amino Groups Obtained by Semicontinuous Seeded Cationic Emulsion Polymerization*, J. of Polymer Science, Plymer chemistry, vol. 43, pp. 3878-3886 (2005).
Redman, *Clinical Experience with Vasovasostomy Utilizing Absorbable Intravasal Stent*, Urology, vol. XX, No. 11, pp. 59-61 (Jul. 1982).
Refracton Techonolgies, Corp., *Fine Bubble Diffusers*, 2 pages (do date).
Refracton Techonolgies, Corp., *Refractron Advanced Porous Ceramic Product Capabilities*, http://www.refractron.com/ecom/sp/cat=Product+Information, printed Apr. 6, 2004, 3 pages.
Refracton Technologies Corp., http://www.refractron.com/ecom/sp/cat=Custom+Applications, printed Jun 24, 2003, 1 page.
Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).
Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).
Saotome, et al., *Novel Enzymatically Degradable Polymers Comprising α-Amino Acid, 1,2-Ethanediol, and Adipic Acid*, Chemistry Letters, pp. 21-24, (1991).
Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).
Schmidt et al., *Long-term Implants of Parylene-C Coated Microelectrodes*, Medical & Biological Engineering & Computing, pp. 96-101 (Jan. 1988).
Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).
Serruys et al., *I Like the Candy, I Hate the Wrapper; the $^{32}P$ Radioactive Stent*, Circulation, vol. 101, pp. 3-7 (Jan. 2000).
Shamim et al., *Measurement of electron emission due to energetic ion bombardment in plasma source ion implantation*, J. Appl. Phys., vol. 70, No. 9, pp. 4756-4759 (Nov. 1991).
Shamim et al., *Measurements of Spatial and Temporal Sheath Evolution for Spherical and Cylindrical Geometrics in Plasma Source Ion Implantation*, J. Appl. Phys., vol. 69, No. 5, pp. 2904-2908 (Mar. 1991).
Shigeno, *Prevention of Cerebrovascular Spasm by Bosentan, Novel Endothelin Receptor*, Chemical Abstract 125:21230 (1996).
Sono Tek Corporation, *AccuMistn™ for Single Stent Coating Applications*, http://www.sono-tek.com/biomedical/accumist_stent.html, printed Aug. 2, 2005, 3 pages.
Sono Tek Corporation,*MediCoat™ DES 1000, Benchtop Stent Coating System*, http://www.sono-tek.com/biomedical/medicoat_standalone.html, printed Aug. 2, 2005, 4 pages.
Sono Tek Corporation, *MicroMist for Stent Coating*, http://www.sono-tek.com/biomedical/micromist_stent.html, printed Aug. 2, 2005, 3 pages.
Spagnuolo et al., *Gas 1 is induced by VE-cadherin and vascular endothelial growth factor and inhibits endothelial cell apoptosis*, Blood, vol. 103, No. 6, pp. 3005-3012 (2004).
Specialty Coating Systems, Inc., *The Parylene Press*, 4 pages (Summer 1993).
Specialty Coating Systems, Inc., *The Parylene Press*, 6 pages (Spring 1993).
Specialty Coating Systems, Inc., *The Parylene Press*, 7 pages (Winter 1992).
Specialty Coating Systems, *Parylene and Nova Tran™ Parylene Coating Services, for Unmatched Conformal Coating Performance*, 21 pages (no date).
Specialty Coating Systems, *Parylene, a Biostable Coating for Medical Applications*, 6 pages (no date).
Specialty Coating Systems, *Repair and Recoating of Parylene Coated Printed Circuit Boards*, 15 pages (no date).
Straube, *Moisture, Materials, & Buildings*, HPAC Engineering, pp. 2-7 (no date).
Taher, *Capillary interaction between a small thin solid plate and a liquid*, Mechanical and Industrial Engineering, University of Illinois at Urbana-Champaign, 4 pages (no date).
Tamai et al., *Initial and 6-Month Results of Biodegradable Poly-I-Lactic Acid Coronary Stents in Humans*, Circulation, vol. 102, pp. 399-404 (2000).
Trident, Inc., http://www.tridentintl.com/subbody.html, printed Dec. 18, 2000, 1 page.
Trident, Inc., *Product Lines*, http://www.tridentintl.com/products-apps/ultrajet.html, printed Dec. 18, 2000, 3 pages.
Tsuji et al., *Biodegradable Polymeric Stents*, Current Interventional Cardiology Reports vol. 3, pp. 10-17 (2001).
Union Carbide Adhesion Promoters, *Union Carbide A-174 Silane*, 5 pages (Jan. 1968).
Union Carbide Electronics Division, *Parylene Environmentally Compatible Conformal Coatings for Electronic Components Assemblies and Precision Parts*, 14 pages (no date).
Union Carbide, *Abrasion Resistance of Parylene and Other Conformal Circuit Board Coatings*, Parylene Products, No. 4, 13 pages (Oct. 1977).
Union Carbide, *Adhesion Promotion Systems for Parylene*, Parylene Products, No. 15, Revision 1, 8 pp. (Oct. 1977).
Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).
Union Carbide, *Fluorescent Parylene Coatings*, Parylene Products, No. 7 Revision 1, 8 pages (Oct. 1977).
Union Carbide, *Fluorescent Parylene Coatings*, Technology Letter, No. 7, 8 pages (Oct. 1973).
Union Carbide, *Mechanical Protection Criteria for Thin Conformal Coatings*, Parylene Products, No. 3, 21 pages (Oct. 1977).
Union Carbide, *Method for Repair and Patching of Parylene Coated Printed Circuit Boards*, Parylene Products, No. 2 Revision 1, 9 pages (Oct. 1977).
Union Carbide, *Microencapsulation by Vapor Deposition*, Parylene Products, No. 6, 12 pages (Oct. 1977).
Union Carbide, *MIL 146058, Qualification of Parylene N, C, and D*, Parylene Products, No. 1 Revision 2, 8 pages (Oct. 1977).
Union Carbide, *Parylene Bibliography*, Parylene Products, No. 5, Revision 4, 17 pages (Jan. 18, 1982).
Union Carbide, *Parylene Conformal Coatings for Hybrid Microelectronics*, Parylene Products, No. 9, 23 pages (Oct. 1973).
Union Carbide, *Parylene Pellicles for Space Applications*, Parylene Products, No. 10, 50 pages (Oct. 1977).
Union Carbide, *Parylene Pyrolysis Kinetics*, Parylene Products, No. 11, 12 pages (Oct. 1977).
Union Carbide, *Parylene Pyrolysis Kinetics*, Technology Letter, No. 11, 12 pages (May 1974).
Union Carbide, *Parylene Removal with Oxygen Plasmas*, Parylene Products, No. 18, 7 pages (Aug. 1977).
Union Carbide, *Printed Circuit Board Masking Techniques for Use with Parylene*, No. 14, Revision 1, 11 pages (Oct. 1977).
Union Carbide, *Solvent Resistance of the Parylenes*, Parylene Products, No. 12, Revision 1, 5 pages (Oct. 1977).
Union Carbide, *The Selective Removal of Parylene by Plasma Etching*, No. 13, Revision 1, 7 pages (Oct. 1977).
Union Carbide, *Thermal Endurance of the Parylenes in Air*, Parylene Products, No. 16, 4 pages (Mar. 1976).
Union Carbide, *Vapor Phase Adhesion Promotion Systems*, Parylene Products, No. 17, Revision 1, 11 pages (Oct. 1977).
van Beusekom et al., *Coronary Stent Coatings*, Coronary Artery Disease, vol. 5, No. 7, pp. 590-596 (Jul. 1994).
van der Giessen et al., *"Edge Effect" of $^{32}P$ Radioactive Stents is Caused by the Combination of Chronic Stent Injury and Radioactive Dose Falloff*, Circulation, vol. 104, pp. 2236-2241 (Oct. 30, 2001).
Vapor Inc., Vapore-Jet™ Capillary Pump—How it Works, http://www.vapore.com/tech_howto.htm, printed Aug. 13, 2003, 2 pages.
Völkel et al., *Targeting of immunoliposomes to endothelial cells using a single—chain Fv fragment directed against human endoglin (CD105)*, Biochemica et Biophysica Acta, vol. 1663, pp. 158-166 (Apr. 15, 2004).

von Recum et al., *Degradation of polydispersed poly(L-lactic acid) to modulate lactic acid release*, Biomaterials, vol. 16, pp. 441-445 (1995).
Welch, Van Gemert, *Optical-Thermal Response of Laser-Irradiated Tissue*, book, (1995).
Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).
Wilensky et al., *Methods and Devices for Local Drug Delivery in Coronary and Peripheral Arteries*, Trends Cardiovasc. Med., vol. 3, No. 5, pp. 163-170 (1993).
Wong et al., *An Update on Coronary Stents*, Cardio, 8 pages (Feb. 1992).
World Precision Instruments, Inc., http://www.wpiinc.com/WPI_Web/Pumps/pneumatic_Fid.gif, printed Sep. 30, 2002, 1 page.
World Precision Instruments, Inc., *Nanoliter Injector*, http://www.wpiinc.com/WPI_Web/Microiniection/Nanoliter_Injector html, printed Jun. 10, 2005, 3 pages.
World Precision Instruments, Inc., *Nanoliter Injector*, http://www.wpi-europe.com/products/microinjection/nanoliter.htm prited Jun. 10, 2005, 2 pages.
World Precision Instruments, Inc., *Pneumatic PicoPumps*, http://www.wpieurope.com/products/microinjection/picopumps.htm, printed Jun. 10, 2005, 4 pages.
World Precision Instruments, Inc., *Pneumatic PicoPumps*, http://www.wpiinc.com/WPI_Web/Microinjection/Pneumatic_PicoPumps.html, printed Jun. 10, 2005, 4 pages.
Yau et al., *Modern Size-Exclusion Liquid Chromatography*, Wiley-Interscience Publication, 9 pages (1979).
Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).
Yuen et al., *Tissue response to potential neuroprosthetic materials implanted subdurally*, Biomaterials, vol. 8, pp. 57-62 (Mar. 1987).
Zhmud et al., *Dynamics of Capillary Rise*, Journal of Colloid and Interface Science, vol. 228, pp. 263-269 (2000).
Zimarino et al., *Analysis of Stent Edge Restenosis with Different Forms of Brachytherapy*, The American Journal of Cardiology, vol. 89, pp. 322-325 (Feb. 1, 2002).
Zylberman et al., *Comparative Study of Electroless Co(W,P) and Co(Mo,P) Thin-Films for Capping and Barrier Layers for Cu Metallization*, 2002 Advanced Metallization Conference, 2 pages (no date).
International Search Report for PCT/US2007/014657, filed Jun. 21, 2007, mailed May 2, 2008 11 pgs.

* cited by examiner

NANOSHELLS ON POLYMERS

BACKGROUND OF THE INVENTION

1. Field of the Invention

The present invention generally relates to a method of forming a nanoshell on a polymeric material, in particular a biodegradable polymeric material.

2. Description of Related Art

Nanoshell technology has attracted much attention because of the potential it offers in therapeutics with or without a therapeutic substance. For example, nanoshells have been demonstrated to absorb and convert light into heat, which can be used to offer local delivery of a drug or local treatment of an injury. Methods of forming nanoshells have been focused on forming them on a core material such as nanoparticulate inorganic ceramics or polymers such as polystyrene. For example, U.S. Pat. No. 6,685,986 is directed to a method of forming metal nanoshells upon a core substrate. The core substrate can be particles of silicon dioxide, titanium dioxide, poly(methyl methacrylate) (PMMA), polystyrene, gold sulfide, macromolecules such as dendrimers, and semiconductors such as Cd Se, Cd S, or GaAs. The particles can further have polyvinyl alcohol (PVA), latex, nylon, Teflon, acrylic, Kevlar, epoxy, glasses (col. 4, line 39 to col. 5, line 33). These core substrates, particularly those polymeric core materials, are generally non-degradable materials.

Therefore, there is a need for forming nanoshells upon a core material which is degradable.

The embodiments described below address the above-identified problems.

SUMMARY

The present invention provides a method of forming nanoshells on a polymeric core substrate. The nanoshell can be a thin layer formed on the polymeric core material. The nanoshell can have a thickness from about 5 nm to about 50 nm, e.g., about 5 nm to about 25 nm. The core substrate can have a size between about 100 nm to about 2000 nm, e.g., between about 100 nm and 50 nm.

The nano-constructs described herein have nanoshells formed on a core material. The nanoshells include a metal, carbon, or a conducting polymer. The nano-constructs can be administered to a target tissue of a subject, which can be human or an animal. An energy source can then be applied to the nano-constructs. The nano-constructs absorb the energy and then translate the energy into heat, thereby providing therapy to the subject.

In some embodiments, where the nano-constructs include one or more bioactive agents (e.g., a drug), the nano-constructs can convert energy into heat so as to cause the bioactive agents to be released. In some embodiments, the nano-construct can include a nanoshell that is porous to the bioactive agent or can be caused to form pores by heat generated by the interaction of the energy with the nano-construct. The nano-constructs can be used to treat or to ameliorate a vascular condition such as atherosclerotic plaque. Other vascular conditions that can be treated or ameliorated include, but are not limited to, vulnerable plaque, vascular inflammation, diffuse atherosclerotic disease, or restenosis.

DETAILED DESCRIPTION

The present invention provides a method of forming nanoshells on a polymeric core substrate. The nanoshell can be a thin layer formed on the core substrate formed of the polymeric core material. The nanoshell can have a thickness from about 5 nm to about 50 nm, e.g., about 5 nm to about 25 nm. The core substrate can have a size between about 100 nm to about 2000 nm, e.g., between about 100 nm and 150 nm.

The nano-constructs described herein have nanoshells formed on a core material. The nanoshells include a metal, carbon, or an electrically conductive, organic material such as graphite or a conductive polymer. The nano-constructs can be administered to a target tissue of a subject, which can be human or an animal. An energy source can then be applied to the nano-constructs. The nano-constructs absorb the energy and then translate the energy into heat, thereby providing therapy to the subject.

In some embodiments, where the nano-constructs include one or more bioactive agents (e.g., a drug), the nano-constructs can convert energy into heat so as to cause the bioactive agents to be released. In some embodiments, the nano-construct can include a nanoshell that is porous to the bioactive agent or can be caused to form pores by heat generated by the interaction of the energy with the nano-construct.

The nano-constructs can be used to treat or to ameliorate a vascular condition such as atherosclerotic plaque. Other vascular conditions that can be treated or ameliorated include, but are not limited to, vulnerable plaque, vascular inflammation, diffuse atherosclerotic disease, or restenosis.

In some embodiments, the nanoshells include a metal or an alloy. In some embodiments, the metal or metal alloy can include gold, silver, platinum, palladium, chromium, iridium, biodegradable metals such as iron, iron based alloys, magnesium, magnesium alloys, zinc, calcium, tungsten, alloys based on these metals, or combinations thereof.

In some embodiments, the nanoshells can comprise carbon. In some embodiments, the nanoshells can comprise an electrically conductive, organic material such as graphite or a conductive polymer. Conductive polymers can be, for example, poly(pyrrole), poly(thiophene), poly(acetylene), poly(aniline), graphite, carbon nanotubes, DNA or combinations thereof. The term conductive polymer can be used interchangeably with the term "conductive polymer."

The nanoshells have a thickness in the range between about 2 nm and about 100 nm. Thickness of the shells and the ratio of core to shell dimension is relevant to the frequency of electromagnetic radiation or irradiation that the shells can absorb and translate into heat. For example, for nanoshells formed of a metal such as gold, the wavelength at which extinction efficiency is largest shifts to longer wavelengths as core-to-shell ratios increase, i.e. as shell thickness decreases if the outer diameter is kept constant. Most relevant, the nanoshells can be designed such that they absorb radiation energy in the near-infrared spectrum between 650 nm and 900 nm which is permeable for tissue (see, e.g., Oldeburg S. J., et al., Applied Physics Letters; Vol. 75(19): 2897-2899; Oldenburg S. J., et al., Chemical Physics Letters 288:243-247 (1998)).

The nano-constructs described herein can be delivered to a subject for treating or ameliorating a vascular condition such as atherosclerotic plaque. Upon delivery, the nano-constructs can reach the target site via passive targeting or active targeting. Passive targeting can be achieved by extravasation of the nano-construct through leaky vasculature such as those present in atherosclerotic plaque. In some embodiments, the result of passive targeting can be assessed by the circulation time of the nano-constructs after delivery. Generally, the longer the nano-constructs remain in circulation, the more nano-constructs can reach the target site or target tissue, which sometimes is also referred to as the diseased site or diseased tissue. Therefore, in some embodiments, passive targeting can be enhanced by increasing nano-construct circulation times by rendering the surface of the nano-construct disguisey using a compound such as poly(ethylene glycol). Other compounds that can be used to hide the nano-constructs include, but are not limited to, hyaluronic acid, phosphoryl choline, dextran, dextrose, sulfo betaine, polypyrrolidone, poly(2-hydroxyethyl methacrylate), albumin, poly(acrylic acid), and poly(methacrylic acid) and PVA.

Extravasation of the nano-constructs is also related to the position and nature of the diseased tissue. The capillary walls of tumor vasculature and the inflamed vasculature of diseased tissue is leaky compared to normal tissue. In some embodiments, extravasation can be achieved by circulation of the nano-constructs in the blood stream for a period from 10 minutes to 120 hours, more specifically from about 4 hours to 48 hours.

In some embodiments, the targeting can be achieved by active targeting. Active targeting can be carried out by attaching a targeting molecule on the nano-constructs (e.g., nanoshells). Targeting molecules include any peptide, antibody, or polysaccharide that has affinity to the target tissue or target site (e.g., atherosclerotic plaque). In some embodiments, the targeting molecule can be a surface-conjugated ligand to a receptor on an inflamed endothelium. Some examples of the targeting molecules are antibodies to CD34, RGD, YIGSR, peptides and antibodies to IIbIIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

The result of active targeting can be assessed by measuring the quantity of nano-constructs in the targeted tissue (i.e. vessel wall) versus the quantity administered. Similar to passive targeting, in some embodiments, the result of active targeting can be assessed by the circulation time of the nano-constructs after delivery. Generally, the longer the nano-constructs remain in circulation, the more nano-constructs can reach the target site. Therefore, in some embodiments, active targeting mediated by a targeting moiety can be enhanced by increasing nano-construct circulation times by modifying the surface of the construct using compounds such as poly(ethylene glycol), hyaluronic acid, phosphoryl choline, dextran, dextrose, sulfo betaine, poly(vinyl alcohol) (PVOH), polypyrrolidone, poly(2-hydroxyethyl methacrylate), albumin, poly(acrylic acid), poly(methacrylic acid) and PVA, whereby the organism's immunological processes fail to recognize the nano-construct as foreign.

Active targeting of the nano-constructs is also related to the position and nature of the diseased tissue. Nano-constructs can reach diseased tissue, which is highly vascularized, by systemic administration. Diseased tissue protected by the blood-brain barrier, which can prevent penetration of the nano-constructs, could be more advantageously accessed by administration into cerebro-spinal fluid. If a high concentration of nano-constructs is desired in the vessel wall of a portion of vascular system, then local delivery using a catheter may be suitable. Some target tissues such as the eye or prostate can be accessed externally by direct injection. In some embodiments, active targeting can be achieved by circulating the nano-constructs in the blood stream for a period from 10 minutes to 120 hours, more specifically from about 4 hours to 48 hours.

For those nano-constructs that include bioactive agents, the bioactive agent can be included in the core material in the form of core-material-drug matrix. Alternatively, the bioactive agent can be included in a substrate to which the nano-construct described herein is conjugated. For example, the substrate can be a nano- or micro-particle or capsule including the bioactive agent. The heat generated from the nano-construct can cause the bioactive agent to release from the substrate. The substrate to which the nano-construct is conjugated can be formed of the same of different material of the polymeric core material of the nano-construct. In some embodiments, the substrate is a self-assembled molecule such as liposomes containing phospholipids, micelles, or polymersomes. Examples of such self-assembled molecules include, but are not limited to, a liposome such as a small unilamellar vesicle (SUV), a large unilamellar vesicle (LUV), a polymersome, or hybrid vesicle comprising a polymer constituent(s). vesicle (LUV), a polymersome, or hybrid vesicle comprising a polymer constituent(s). Finally, the bioactive agent can be included in the shell of the nano-construct. Those of ordinary skill in the art recognize that these various locations for the bioactive agent are not exclusive. Thus, in some embodiments the bioactive agent can be present in any combination of core, substrate, or shell.

Polymeric Core Materials

The core material can be any polymeric material. Preferably, the core substrate can be formed of a material that comprises a biodegradable polymer. Also, it is preferable for the core polymeric material to have dielectric properties. In some embodiments, the core material can be a non-degradable polymer. As used herein, a degradable polymer is a polymer having a backbone that comprises at least one degradable linkage or grouping in the backbone, and a non-degradable polymer is a polymer having a backbone that lacks a backbone degradable linkage or grouping. Degradable linkages or groupings include a bond that can be cleaved by hydrolysis or enzymatic cleavage. An example of a degradable linkage or grouping is an ester linkage. An example of the non-degradable polymers is a polymer formed of vinyl monomers.

Representative polymeric core materials include poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof.

In some embodiments, the polymeric core material can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

In some embodiments, the core material can include ferromagnetic or magnetic ceramic particles.

Bioactive Agents

The nanoshells described herein can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration and proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin(everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Methods of Forming Nanoshells

Nanoshells can be formed on a core material using established methods. For example, U.S. Pat. No. 6,699,724 describes forming conducting nanoshells on a non-conducting core. The size and thickness of the core/shell can be tuned so that the particles can absorb light with a desired wavelength. Biomolecules such as proteins or peptides can be attached to the nanoshells for binding to a specific tissue.

U.S. Pat. No. 6,685,986 describes a method of forming metal nanoshells upon a core substrate. The nanoshells can be formed of a metal such as gold or a conducting polymer. The core substrate can be particles of silicon dioxide, titanium dioxide, alumina, zirconia, poly(methyl methacrylate) (PMMA), polystyrene, gold sulfide, macromolecules such as dendrimers, semiconductors such as CdSe, CdS, or GaAs. The particles can further have polyvinyl alcohol (PVA), latex, nylon, Teflon, acrylic, Kevlar, epoxy, or glasses. Some other references, for example, U.S. application publication Nos. 2003/0164064, 2002/0061363, 2002/0187347, 2002/0132045, and 2005/0056118, also describes various methods of forming metal nanoshells on a core substrate. Formation of partial nanoshells can be according to the method described in, for example, U.S. Pat. No. 6,660,381.

In some embodiments, the nanoshells can be formed via metal colloidal nanoparticles such as colloidal gold nanoparticles. For example, colloidal gold nanoparticles of 3-4 nm size can assemble on nanoparticle surfaces functionalized by amine groups. These nanoparticles act as nucleation sites, and when a gold salt is present in a reducing environment, a solid gold shell can be formed around this type of nanosize template such as a nanosphere.

In some embodiments, polymeric nanoparticles such as commercially available polystyrene particles modified at their surface to present amine groups may be used as a template for gold nanoshells. Amine functionality can be placed onto these polymers by a variety of techniques. For example, polymeric surface can be modified to have amine functionality via plasma treatment in the presence of ammonia or hydrazine. This plasma process can be carried out on preformed nanoparticles by agitating them in a plasma reactor. Amino groups can also be incorporated into the end-groups of a polymer (e.g., a biodegradable polymer), if the initiator contains both a hydroxyl group and an amino group protected by a carbobenzoxy group or a t-butoxycarbonyl group, and this initiator is used to make a biodegradable polymer by ring opening polymerization, such as poly(L-lactide) or polyglycolide. After the polymerization, the protecting group can be removed, liberating the amino group. Polymeric methacrylates can be made with amino groups by using a monomer such as N-(3-aminopropyl)methacrylamide. A copolymer with other monomers such has butyl methacrylate or methyl methacrylate can be made. In some embodiments, a dispersion or emulsion polymerization process can be used to form monodisperse nanoparticles with surface amino groups (see, e.g., Ramos; Jose, Forcada; Jacqueline. Polymer 47(4):1405 (2006); Ramos; Jose, Forcada; Jacqueline, Polymer Chemistry 43 (17):3878 (2005); Prakash, G. K. et al., J. of Nanoscience and Nanotechnology 5(3):397 (2005); and Musyanovych, Anna; Adler, Hans-Jurgen Organic Chemistry III Macromolecular Society, 21(6):2209 (2005).

In some embodiments, the nanoshells can be formed via thiol-group-facilitated nanoparticle assembling. For example, biodegradable poly(propylene sulfide) can be produced in nanoparticle form as shown by Annemie Rehor (Ph. D. thesis, Swiss Federal Institute of Technology, Zurich, 2005). This polymer has thiol end-groups from the polymerization, which can be maximized in number by exposing the nanoparticles to reducing conditions.

In some embodiments, the nanoshells can be modified to include a targeting molecule. The target molecule can be any peptides or antibodies such as ligands for receptors on an inflamed endothelium. Examples of such targeting molecules include, but are not limited to, antibodies to CD34, RGD, YIGSR, peptides and antibodies to IIbIIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

Attachment of targeting molecule to nanoshells can be achieved by established methods. The targeting molecule can be attached to the nanoshell via covalent bonding or non-covalent interaction. Non-covalent interaction can be based on ionic interaction, hydrogen bonding or other type of interaction. For example, after formation of the gold nanoshell, molecules functionalized with a thiol group can be used to modify the nanoshell surface for targeting of the nanoshell, or to disguise the nanoshell surface. Thiol-terminated molecules have been shown to self-assemble on gold surfaces. For example, thiol-terminated poly(ethylene glycol) (PEG) having a molecular weight of about 200 Daltons to 10,000 Daltons, preferably between 500 Daltons to about 2,000 Daltons can be used to disguise the nanoshell surface. The other end of the PEG chain can be functionalized with a targeting molecule such as a peptide or an antibody to target the nanoshell to specific tissue within the body.

In some embodiments, the targeting molecule can be attached to a nanoshell via a spacer. A spacer molecule can be a short-chain alkyl group such as a C1-C20 alkyl, C3-C20 cycloalkyl, poly(ethylene glycol), poly(alkylene oxide). Other spacer molecules include dextran, dextrose, heparin, poly(propylene sulfide), hyaluronic acid, peptides, DNA, PVA and PVP.

Method of Use

The nano-constructs provided herein can be delivered or administered to a subject via any established mode of delivery. For example, the nano-constructs can be delivered by systemic delivery such as systemic injection. In some embodiments, the nano-constructs can be administered by local delivery such as direct injection. For disorders of the vascular system, the nano-constructs may be administered by catheter-based devices. These would include single and dual needle injection catheters, porous balloon catheters, balloon catheters with jets, and double balloon catheters. In general, the nano-constructs of this invention do not rely on any particular delivery method.

Upon delivery to the target tissue, an energy source can be applied to the nano-constructs. The nano-constructs can then absorb the energy and convert it or translate it to heat so as to warm or ablate the diseased tissue. The energy source can be in any form capable of reaching the nano-constructs and being absorbed and converted by the nano-constructs into heat. In some embodiments, the energy source can be applied through external radiation or through a catheter-based guidance system.

In some embodiments, the energy source is an electromagnetic radiation having a wave length from 500 nm to 1500 nm. For example, the energy source can be a near infrared radiation.

In some embodiments, the energy source is a fluctuating electromagnetic field. Such electromagnetic field can have a frequency from $1 \times 10^6$ Hz to $6 \times 10^{14}$ Hz. In some embodiments, the electromagnetic field can have a frequency of 700 nm to 1300 nm where optical transmission is optimal (Welch A.; van Gemert, M. e. *Optical-Thermal Response of Laser Irradiated Tissue*, Plenum Press: New York, 1995).

In some embodiments, the energy source can be applied to the nano-constructs by a catheter-based fiber-optic. The localization of plaque can be imaged prior to the procedure or during the procedure by interrogation with an attenuated radiation. For example, the plaque may be imaged by optical coherence tomography using a wavelength of 1300 nm (Meissner O. A., et al. J Vasc Interv Radiol 2006; 17: 343-349) or intravascular ultrasound (Colombo et al., Circulation, 91:1676-88 (1995)). This same wavelength could then be used to apply energy to the nano-constructs after they are administered.

The nano-construct described herein can be used to treat, prevent or ameliorate a medical condition. Such a medical condition can be, e.g., a tumor or nephropathic kidney. In some embodiments, such a site can be a site of atherosclerosis. Other medical conditions treatable using invention processes or nanoconstructs include vulnerable plaque, diffuse atherosclerotic disease, diabetic retinopathy, aneurysm, anastomotic hyperplasia, claudication, chronic total occlusion, dysfunctional endothelium, recurring thrombus, fibrin accumulation, or combinations of these.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:
1. A nano-construct comprising:
   (a) a core material comprising a polymer,
   (b) a nanoshell formed on the core material, and
   (c) a bioactive agent,
   wherein the polymer is a degradable polymer selected from the group consisting of a polyester, poly(ester amide), polyether, polyanhydride, polyorthoester or a non-degradable polymer selected from the group consisting of poly(N-(3-aminopropyl)methacrylamide), a copolymer of N-(3-aminopropyl)methacrylamide, and a combination of these, and
   wherein the nanoshell comprises a metal having a thickness from about 5 nm to about 50 nm selected from the group consisting of gold, iron, magnesium, zinc, calcium, tungsten, alloys based on these metals, and combinations thereof.

2. The nano-construct of claim 1 wherein the nanoshell comprises gold.

3. The nano-construct of claim 2 wherein the gold nanoshell has a thickness between about 5 nm and about 25 nm.

4. The nano-construct of claim 1 wherein the core material has a size in the range between about 150 nm to about 2000 nm.

5. The nano-construct of claim 1 wherein the nanoshell on the core material is porous to the bioactive agent.

6. The nano-construct of claim 1 wherein the nanoshell comprises iron, magnesium, zinc, calcium, tungsten, alloys based on these metals, or combinations thereof.

7. The nano-construct of claim 1 wherein the nanoshell comprises an electrically conductive, organic material.

8. The nano-construct of claim 1 wherein the nanoshell comprises graphite or a conductive polymer.

9. The nano-construct of claim 1 wherein the nanoshell comprises poly(L-lactide), polyhydroxyalkanoate, polycaprolactone, or combinations thereof.

10. The nano-construct of claim 1 further comprising a substrate that includes the bioactive agent.

11. The nano-construct of claim 10 wherein the substrate is a small unilamellar vesicle (SUV) encapsulating the bioactive agent.

12. The nano-construct of claim 10 wherein the substrate is a liposome, polymersome, or hybrid vesicle.

13. The nano-construct of the claim 1 wherein the core material further comprises ferromagnetic or magnetic ceramic particles.

14. The nano-construct of claim 1 wherein the core material comprises a peptide, a protein, or a combination of these.

15. The nano-construct of claim 1 further comprising a targeting molecule on the surface of the nano-construct.

16. The nano-construct of claim 15 wherein the targeting molecule is a surface-conjugated ligand for receptors on an inflamed endothelium.

17. The nano-construct of claim 1 in a formulation suitable for systemic delivery or local delivery into a human being.

18. The nano-construct of claim 17 wherein the systemic delivery is injection.

19. The nano-construct of claim 17 wherein the local delivery is delivery by a device comprising a catheter.

20. The nano-construct of claim 1 wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N-1-tetrazolyl)-rapamycin (ABT-578), γ-hirudin clobetasol, pimecrolimus, imatinib mesylate, midostaurin, prodrugs thereof, co-drugs thereof, and combinations of these.

21. A method of forming a nano-construct, comprising:
   forming a nanoshell on a core material comprising a polymer, and incorporating at least one bioactive agent with the nanoshell or the core material, wherein the polymer is a degradable polymer or a non-degradable polymer, the non-degradable polymer is selected from the group consisting of poly(N-(3-aminopropyl)methacrylamide), a copolymer of N-(3-aminopropyl)methacrylamide, and a combination of these; and wherein the nanoshell comprises a metal having a thickness from about 5 nm to about 50 nm selected from the group consisting of gold, iron, magnesium, zinc, calcium, tungsten, alloys based on these metals, and combinations thereof.

22. The method of claim 21 wherein the core material encapsulates at least one bioactive agent.

23. The method of claim 21 wherein the nanoshell is porous.

24. The method of claim 21 further comprising connecting the nano-construct to a substrate.

25. The method of claim 24 wherein the substrate comprises a self-assembled structure.

26. The method of claim 21 wherein the nanoshell comprises gold and has a thickness between about 5 nm and about 25 nm.

27. The method of claim 21 wherein the nanoshell consists essentially of gold and has a thickness between about 5 nm and about 25 nm.

28. The method of claim 21 wherein the core material has a size between about 150 nm and about 2000 nm.

29. The method of claim 21 wherein the core material comprises a peptide, a protein, or a combination of these.

30. The method of claim 21 wherein the nano-construct comprises a targeting molecule on the surface of the nano-construct.

31. The method of claim 29 wherein the targeting molecule is a surface-conjugated ligand for receptors on an inflamed endothelium.

32. The method of claim 21 wherein the nano-construct is in a formulation suitable for systemic delivery or local delivery into a human being.

33. The method of claim 32 wherein the systemic delivery is injection.

34. The method of claim 32 wherein the local delivery is delivery by a device comprising a catheter.

35. The method of claim 21 wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N-1-tetrazolyl)-rapamycin (ABT-578), γ-hirudin, clobetasol, pimecrolimus, imatinib mesylate, midostaurin, prodrugs thereof, co-drugs thereof, and combinations of these.

36. A method of treating, preventing, or ameliorating a medical condition, comprising:
delivering to a disease site in the body of a human being in need of treatment the nano-construct of claim 1,
wherein the nano-construct releases the bioactive agent.

37. The method of claim 36 wherein the bioactive agent is released by radiating the nano-construct with radiation, and wherein the nano-construct converts the radiation into heat.

38. The method of claim 37 wherein the radiation uses a near infrared (NIR) electromagnetic radiation transmitted through a catheter-based fiber-optic.

39. The method of claim 37 wherein the radiation is electromagnetic and is applied outside the body of the subject.

40. The method of claim 36 wherein the delivering comprises allowing the nano-construct to extravasate through leaky vasculature in the target tissue.

41. The method of claim 36 wherein the nano-construct comprises targeting molecules on the surface of the nano-construct.

42. The method of claim 41 wherein the targeting molecules comprises surface-conjugated ligands for receptors on an inflamed endothelium.

43. The method of claim 36 wherein the nano-construct comprises a surface-disguising compound on the surface of the nano-construct that increases the circulation time of the nano-construct.

44. The method of claim 43 wherein the surface-disguising compound comprises poly(ethylene glycol).

45. The method of claim 36 wherein medical condition is one or more of atherosclerosis, tumor, a nephrosis, vulnerable plaque, diffuse atherosclerotic disease, diabetic retinopathy, aneurysm, anastomotic hyperplasia, claudication, chronic total occlusion, dysfunctional endothelium, recurring thrombus, or fibrin accumulation.

46. The method of claim 36 wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N-1-tetrazolyl)-rapamycin (ABT-578), γ-hirudin, clobetasol, pimecrolimus, imatinib mesylate, midostaurin, prodrugs thereof, co-drugs thereof, and combinations of these.

* * * * *